United States Patent
Kranz et al.

(10) Patent No.: US 8,574,307 B2
(45) Date of Patent: Nov. 5, 2013

(54) JOINT PROSTHESIS SYSTEM

(75) Inventors: Curt Kranz, Berlin (DE); Emmanuel Anapliotis, Berlin (DE); Martin Hilse, Berlin (DE)

(73) Assignee: Merete Medical GmbH (DE)

( * ) Notice: Subject to any disclaimer, the term of this patent is extended or adjusted under 35 U.S.C. 154(b) by 0 days.

(21) Appl. No.: 13/378,613

(22) PCT Filed: Jul. 28, 2010

(86) PCT No.: PCT/DE2010/000881
§ 371 (c)(1),
(2), (4) Date: Dec. 15, 2011

(87) PCT Pub. No.: WO2011/012115
PCT Pub. Date: Feb. 3, 2011

(65) Prior Publication Data
US 2012/0265320 A1 Oct. 18, 2012

(30) Foreign Application Priority Data
Jul. 29, 2009 (DE) .......................... 10 2009 035 259

(51) Int. Cl.
*A61F 2/32* (2006.01)
(52) U.S. Cl.
USPC ..................................................... 623/22.45
(58) Field of Classification Search
USPC .......... 623/22.11, 23.53, 23.41, 23.18, 23.25, 623/23.44, 23.45, 23.52, 22.4, 23.21, 23.35, 623/19.13, 22.45
See application file for complete search history.

(56) References Cited

U.S. PATENT DOCUMENTS

| 4,170,794 | A | * | 10/1979 | Zeibig et al. | 623/22.45 |
| 5,066,304 | A |   | 11/1991 | Crowninshield et al. |   |
| 5,120,488 | A | * | 6/1992 | Borrman et al. | 376/203 |
| 5,362,311 | A | * | 11/1994 | Amino et al. | 623/22.45 |
| 5,865,850 | A | * | 2/1999 | Matthews | 623/22.43 |
| 6,336,941 | B1 | * | 1/2002 | Subba Rao et al. | 623/22.42 |

(Continued)

FOREIGN PATENT DOCUMENTS

| DE | 91 03 574 U1 | 4/1992 |
| DE | 195 17 843 A1 | 11/1996 |

(Continued)

OTHER PUBLICATIONS

International Search Report for parent application PCT/DE2010/000881, having a completion date of Nov. 11, 2010 and a mailing date of Nov. 19, 2010.

*Primary Examiner* — Bruce E Snow
*Assistant Examiner* — Melissa Hoban
(74) *Attorney, Agent, or Firm* — Andrus, Sceales, Starke & Sawall, LLP (57) ABSTRACT

A joint prosthesis system has a metal shaft, which is implanted in the femur, a throat having an outer cone, a joint ball made of ceramic and an accommodation for the throat. The accommodation has an inner cone, and a sheath-shaped adapter, which is arranged between the shaft and the joint ball in a clamping manner. Due to an exceptional elasticity and a special shaping of an inner and outer wall section of the adapter, the application of force to a narrow surface region on the metal outer cone and the application of the force into the ceramic inner cone is extensively concentrated on a load-bearing region (B) opposite the narrow surface region within the largest mass expansion of the ceramic joint ball.

18 Claims, 5 Drawing Sheets

(56) References Cited

U.S. PATENT DOCUMENTS

| | | | |
|---|---|---|---|
| 6,607,560 B1 * | 8/2003 | Pfaff et al. | 623/22.45 |
| 6,797,007 B1 * | 9/2004 | Von Chamier et al. | 623/22.45 |
| 6,802,866 B2 * | 10/2004 | Bunz | 623/22.14 |
| 7,179,297 B2 * | 2/2007 | McLean | 623/22.11 |
| 2002/0151984 A1 * | 10/2002 | White | 623/23.22 |
| 2004/0138757 A1 * | 7/2004 | Nadzadi et al. | 623/22.11 |
| 2006/0188845 A1 | 8/2006 | Serafin et al. | |
| 2008/0058951 A1 * | 3/2008 | Saladino et al. | 623/23.24 |
| 2008/0243264 A1 * | 10/2008 | Fonte | 623/22.43 |

FOREIGN PATENT DOCUMENTS

| | | |
|---|---|---|
| DE | 196 40 745 A1 | 1/1998 |
| DE | 199 04 437 A1 | 8/2000 |
| EP | 0 385 572 A1 | 9/1990 |
| EP | 0 385 572 B1 | 3/1993 |
| EP | 0 562 782 A2 | 9/1993 |
| EP | 1 124 507 A1 | 8/2001 |
| WO | 00/69372 A1 | 11/2000 |

* cited by examiner

FIG. 4

JOINT PROSTHESIS SYSTEM

CROSS-REFERENCE TO RELATED APPLICATIONS

This application is the U.S. national stage application of International Application No. PCT/DE2010/000881, filed Jul. 28, 2010, which International application was published on Feb. 3, 2011 as International Publication No. WO 2011/012115 A1 in the German language and which application is incorporated herein by reference. The International application claims priority of German Patent Application No. 10 2009 035 259.7, filed Jul. 29, 2009, which application is incorporated herein by reference.

The invention relates to a joint prosthesis system comprising a metal shaft which is implanted into the femur and which has a neck having an external cone, a ball of the joint made of ceramic having a receptacle for the neck, said receptacle comprising an internal cone, and an adapter in the form of a sleeve which is arranged between the shaft and the ball of the joint in a press-fitting manner.

PRIOR ART

DE 199 04 437 A1 discloses a press fit connection between prosthesis components of a joint prosthesis, wherein the first prosthesis component is inserted into the bone tissue and bears a cone, upon which is set a spherical head, which articulates with another joint partner which is formed as a socket, wherein a coupling element which is arranged for homogenising the transfer of forces between the cone and the spherical head. The elasticity and the damping properties of this coupling element are provided by its porosity and the structure of its surface. The coupling element can consist of a wound body, a sintered body or a sponge body made of biocompatible material.

This prior art is representative of further known solutions such as for example EP 385 572 E1, DE 91 03 574 U1, DE 195 17 843 A1, DE 196 40 745 A1, EP 1 124 507 A1.

In all these known solutions, the coupling element comes to bear in completely flat contact between the shaft and the ball of the joint, and so the force introduced during movement, which in individual cases can readily reach five times the body weight, is introduced over the entire cone surface of the metal neck and the ceramic ball of the joint in which way the direction of the introduction of the force diverges substantially from the centre point of the ball of the joint. In the case of continuous load, this often leads to failure of the ceramic, i.e. to crack formation and as a result to breakage. Even the smallest cracks cause the dreaded wear in the ceramic-metal material combination, which in the end entails an early corrective operation for the patient.

A further disadvantage is that in particular if during corrective operations the cone angle of the prosthesis neck is unknown and/or the external cone of the prosthesis neck is damaged, an extraction of the prosthesis shaft must be carried out, often despite the shaft being securely located, with all the detrimental consequences for the patient.

STATEMENT OF THE OBJECT

In the light of this prior art, the object of the invention is to provide a joint prosthesis system which is made of a metal/ceramic combination and which enables defects in the angle of the cone on the neck of the prosthesis to be compensated for securely with a concurrent increase in the life of the prosthesis, and enables the ceramic ball of the joint to be set with an exact fit on the neck of a prosthesis even if the cone dimensions of the prosthesis shaft are not known.

This object is achieved by a joint prosthesis system of the generic type referred to above having the features of claim 1.

Advantageous embodiments of the joint prosthesis system according to the invention are set out in the dependent claims.

The solution according to the invention is based on the knowledge that due to a particular elasticity and a special shaping of an inner wall section and an outer wall section of the adapter, the force introduced is concentrated on a narrow surface region on the metal external cone and the force introduced into the ceramic internal cone is concentrated areally on a load-bearing region which is within the thickest part of the ceramic ball of the joint and which faces the narrow surface region.

This is achieved by means of an adapter, which is designed as a conical moulded body, the inner wall section of which has a convex, circumferentially-shaped bulge facing the external cone of the neck for a targeted concentration of the force introduced onto the narrow surface region of the external cone belonging to the upper part of the neck of the shaft, an outer wall section which is of conical design with respect to the internal cone of the ball of the joint and is assigned to the inner wall section for bearing areally against the load-bearing region of the internal cone of the ball of the joint, and an elastic wall section, which initially is supported on the lower part of the external cone below the load-bearing region in order to prevent a twisting torque produced by the convex circumferential bulge and subsequently is elastically supported on the internal cone of the ball of the joint.

This is connected with the extraordinary advantage that the ceramic ball of the joint is only stressed in the region which is very close to the virtual centre point of the ball of the joint and is able to absorb forces to a specific extent. The regions which are located further from the virtual centre point of the ball of the joint are unstressed and only need to counteract the twisting torque of the ball of the joint.

Furthermore it is particularly advantageous if the moulded body consists of a superelastic material, preferably a biocompatible shape-memory alloy, for example nickel-titanium alloy, which demonstrates a pronounced superelasticity, because of which the adapter is subject to hysteresis which returns the adapter to its original shape dependent upon the level of tension acting upon it. The adapter according to the invention is therefore able to maintain its preferred position on the neck of the prosthesis and on the internal cone of the ball of the joint so that force is introduced only to a narrow region on the external cone of the neck and correspondingly on the load-bearing region on the internal cone of the ceramic ball of the joint. In other words, high loads act on the metal external cone, whereas the ceramic internal cone is loaded only slightly on a sufficiently large contact surface so that the ceramic ball of the joint is not endangered.

It has been shown that the moulded body can also consist of a biocompatible titanium alloy.

In a preferred embodiment of the joint prosthesis system according to the invention, the moulded body has at least one cut-out in its longitudinal direction which serves to counteract a change in the the behaviour of the moulded body induced under load.

It has been shown that cut-outs with a slit or v shape are particularly suited to this. Several cut-outs can also advantageously be arranged aligned above each another or staggered with respect to each other on the circumference.

According to a preferred embodiment of the invention, the moulded bodies have correspondingly adapted axial lengths for neck sections of the shaft of differing lengths in order to be able to select the adapter with a suitable length according to the conditions of the operation.

According to a further preferred embodiment of the invention, the moulded bodies have correspondingly adapted diameters and cone angles for differing diameters of neck sections of the shaft and for differing angles of the external cone of the shaft to ensure that the surgeon can correctly select the appropriate superelastic adapter for use corresponding to the angle and diameter deviations actually present for the patient.

In a further preferred embodiment of the invention, moulded bodies with different axial lengths, diameters and angles form groups of adapters, each of which is assigned a sample adapter for identifying a good fit of the shaft and the ball of the joint.

This ensures that the surgeon can identify the suitable adapter quickly and problem-free during the operation.

In an advantageous further embodiment of the invention, the groups of adapters have a corresponding graduation of diameters for shaft diameters of all commercially available prostheses. The graduation allows possible angle defects on the external cone of the neck of commercially available prostheses of different dimensions and from different manufacturers to be compensated for by means of the elastic behaviour of the adapter according to the invention.

In a particularly advantageous arrangement of the invention, a further adapter is provided between the ceramic ball of the joint and the adapter according to the invention so that it becomes possible to use commercially available ceramic balls of the joint with the adapters that belong to them and correspondingly combine them.

Further advantages and details are apparent from the following description with reference to the appended drawings.

EMBODIMENT

The invention will be explained in greater detail below with reference to an embodiment.

Figure 1:
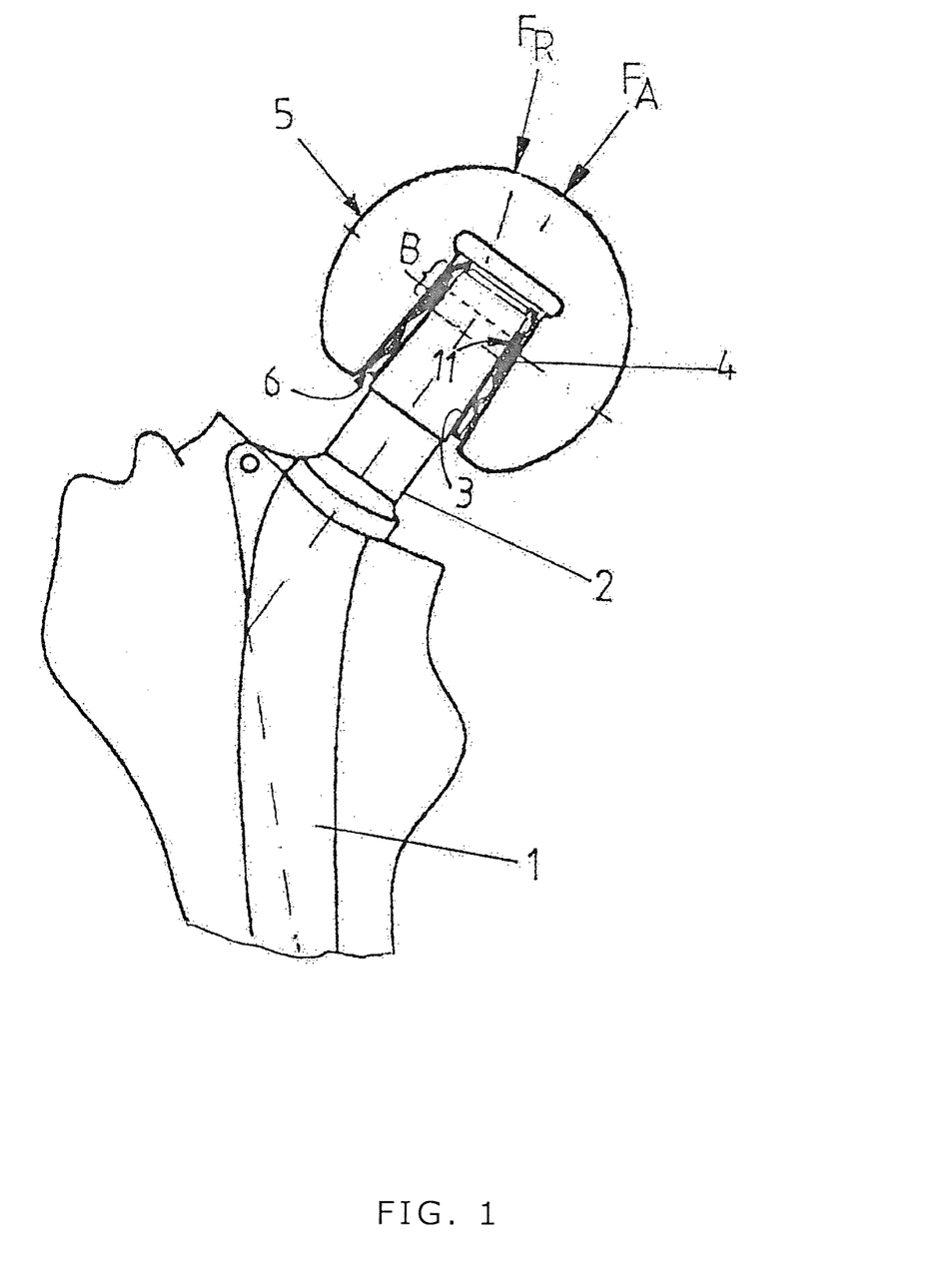
FIG. 1 shows a cross-section through the joint prosthesis system.

FIG. 1 shows a cross-section through the joint prosthesis system according to the invention. The shaft 1 of the joint prosthesis according to the invention is inserted into the medullary cavity of the femur and appropriately adapted to the anatomy of the medullary cavity. A neck 2 having an external cone 3, on which an adapter 4 is fitted, adjoins the shaft 1. The ceramic ball 5 of the joint is provided with a receptacle 6 which is designed as an internal cone 7 (see FIG. 2). The internal cone 7, the adapter 4 and the external cone 3 form a conical plug connection, which is defined by the respective diameters of both the internal and external cones and also the cone angles α and β associated therewith. The resultant physiological force $F_R$ and the axial force $F_A$ acting on the hip joint are indicated schematically in FIG. 1 in order to clarify the effect of the forces on the ceramic ball 5 of the joint. The ball 5 of the joint is best able to support loads where it has the greatest thickness in relation to its virtual centre point (see region B in FIGS. 2a and 2b).

Figure 2A:
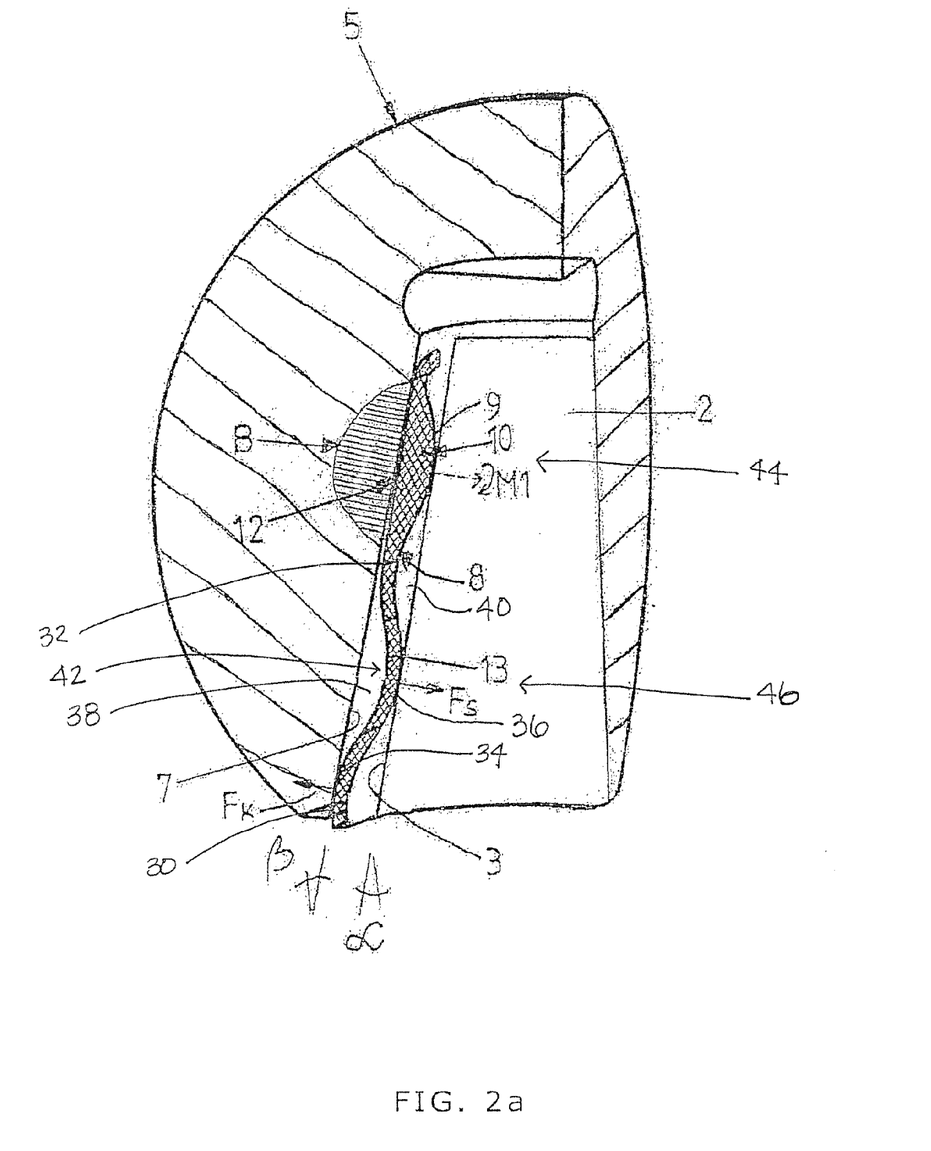
FIGS. 2a and 2b show enlarged views of the adapter between the internal cone of the ceramic ball of the joint and the external cone of the neck of the metal shaft with differing cone angles according to FIG. 1.
Figure 2B:
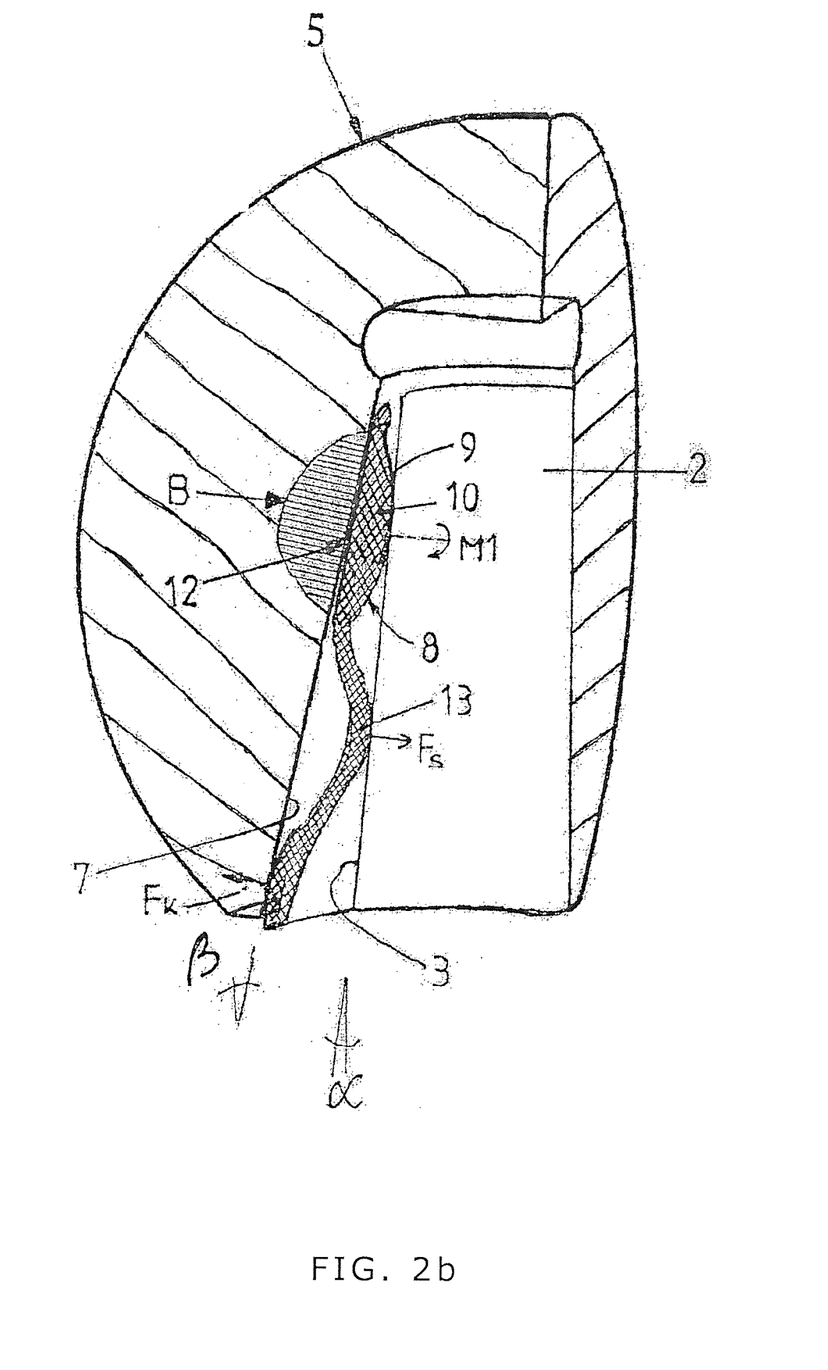

FIGS. 2a and 2b each show an enlarged view of the adapter 4 arranged between the internal cone 7 of the ball 5 of the joint and the external cone 3 of the neck (see also FIG. 1) with differing cone angles α of the external cone 3. The adapter 4 is designed as a moulded body 8 in the form of a sleeve and consists of a biocompatible alloy with shape memory, for example a nickel-titanium alloy such as Nitinol (brand name of the Nickel Titanium Naval Ordnance Laboratory) comprising approximately 50% by weight nickel and the rest titanium. The cone angle β of the internal cone 7 of the ball 5 of the joint is constant.

The adapter 4 therefore has a very high superelastic deformability, high buckling resistance and pronounced hysteric behaviour, as a result of which this material is particularly suitable for press fit connections.

The moulded body 8 of the adapter 4 has an inner wall section 9 which is provided with a circumferential convex bulge 10 facing the external cone 3 of the neck 2 of the shaft 1, said bulge being supported at its highest point on a narrow surface region 11 of the external cone 3 belonging to the upper part of the neck 2. This ensures that the forces acting on the metal side of the press fit connection are concentrated in the narrow surface region.

An outer wall section 12 on the moulded body 8 is assigned to the inner wall section 9, wherein said outer wall section is of conical construction corresponding to the contour of the internal cone 7 of the ceramic ball 5 of the joint and thus by tilting comes to bear in surface contact on the load-bearing region B of the internal cone 7 of the ball 5 of the joint, and so the forces acting on the ball of the joint are uniformly distributed in the load-bearing region. This should be clarified by FIGS. 2a and 2b.

The inner and outer wall sections 9 and 12 each transitions into a elastic wall section 13 which is located below the load-bearing region B and the bulge 10 and is elastically supported on the metal neck 2 of the external cone 3 with a spring force FS, wherein the lower part of the elastic wall section 13 in turn bears elastically on the internal cone 7 of the ball 5 of the joint and absorbs the twisting torque M1 of the ball 5 of the joint due to the spring force FK. The elastic properties of the wall section 13 compensate for any changes in diameter which may occur and/or changes in angle of the metal external cone 3 of the shaft 2 or the prosthesis, wherein the elastic support can be dimensioned in such a way that a break in the ball 5 of the joint can be reliably excluded.

As a result of the superelastic properties of the shape-memory alloy, defects in angle and diameter occurring between the internal cone 3 and external cone 7 are reliably compensated for.

With further reference to FIG. 2a, one embodiment of the adapter 4 will be described. A lowermost end 30 of the adapter 4 bears against the internal cone 7 of the receptacle 6. The elastic wall section 13 is situated above the lowermost end 30 of the adapter 4. At the lowermost end 30 of the adapter 4 is a lower portion 34 of the elastic wall section 13. The lower portion 34 of the elastic wall section 13 bears against the internal cone 7 of the receptacle 6. The elastic wall section 13 then bows radially inwardly toward the external cone 3 of the neck 2 such that a middle portion 42 of the elastic wall section 13 has a surface 36 that bears against the external cone 3 of the neck 2 and an upper portion 32 of the elastic wall section 13 bears against the internal cone 7 of the receptacle 6. This configuration thereby creates at least one gap 38 between the outer wall 12 of the adapter 4 and the internal cone 7 of the receptacle 6. Continuing in an upward direction along the adapter 4, the bulge 10 is situated above the elastic wall section 13. Where the upper portion 32 of the elastic wall section 13 transitions into the bulge 10, at least one gap 40 is formed between the inner wall 9 of the adapter 4 and the external cone 3 of the neck 2.

In other words, the adapter 4 comprises a curvilinear inner wall 9 facing the external cone 3 of the neck 2 and a curvilinear outer wall 12 facing the internal cone 7 of the receptacle 6. The curvilinear inner and outer walls 9, 12 are formed by the shaping of the bulge 10 and the elastic wall section 13 of the adapter 4. The curvilinear inner and outer walls 9, 12 are also formed due to the spacing between the bulge 10, which faces an upper portion 44 of the neck 2, and the elastic wall section 13, which faces a lower portion 46 of the neck 2.

Figure 3:
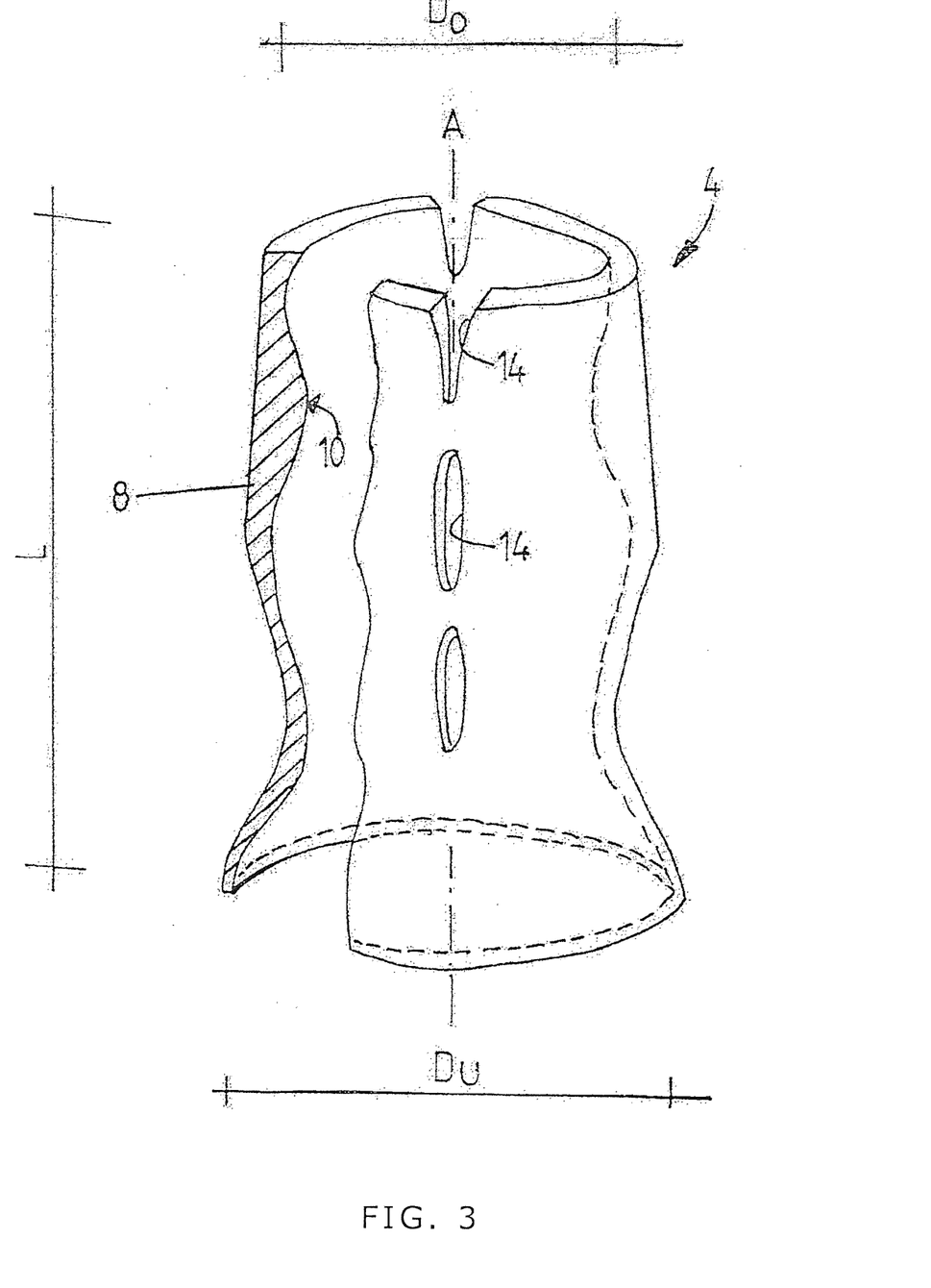
FIG. 3 shows a perspective view of an adapter.

FIG. 3 shows a perspective view of the moulded body 8 in the form of a sleeve. In the longitudinal direction A of the moulded body 8, the moulded body has 3 slit-shaped cut-outs 14 which permit an elastic change in the diameter of the adapter 4. The moulded body 8 is characterised by its conicity, i.e. the change from the upper diameter DO to the lower diameter DU over the length L of the cone.

The internal cone 7 of the receptacle 6 of the ball 5 of the joint and the external cone 3 of the neck 2 of the prosthesis must be adapted to each other. Thus such an interface can be formed from correspondingly graduated pairs of cones with, for example, diameters of 8, 10 or 12 mm for the internal cone and of 10, 12 or 14 mm for the external cone. The cone angle $\alpha$ is between 4.5 and 7°.

Figure 4:
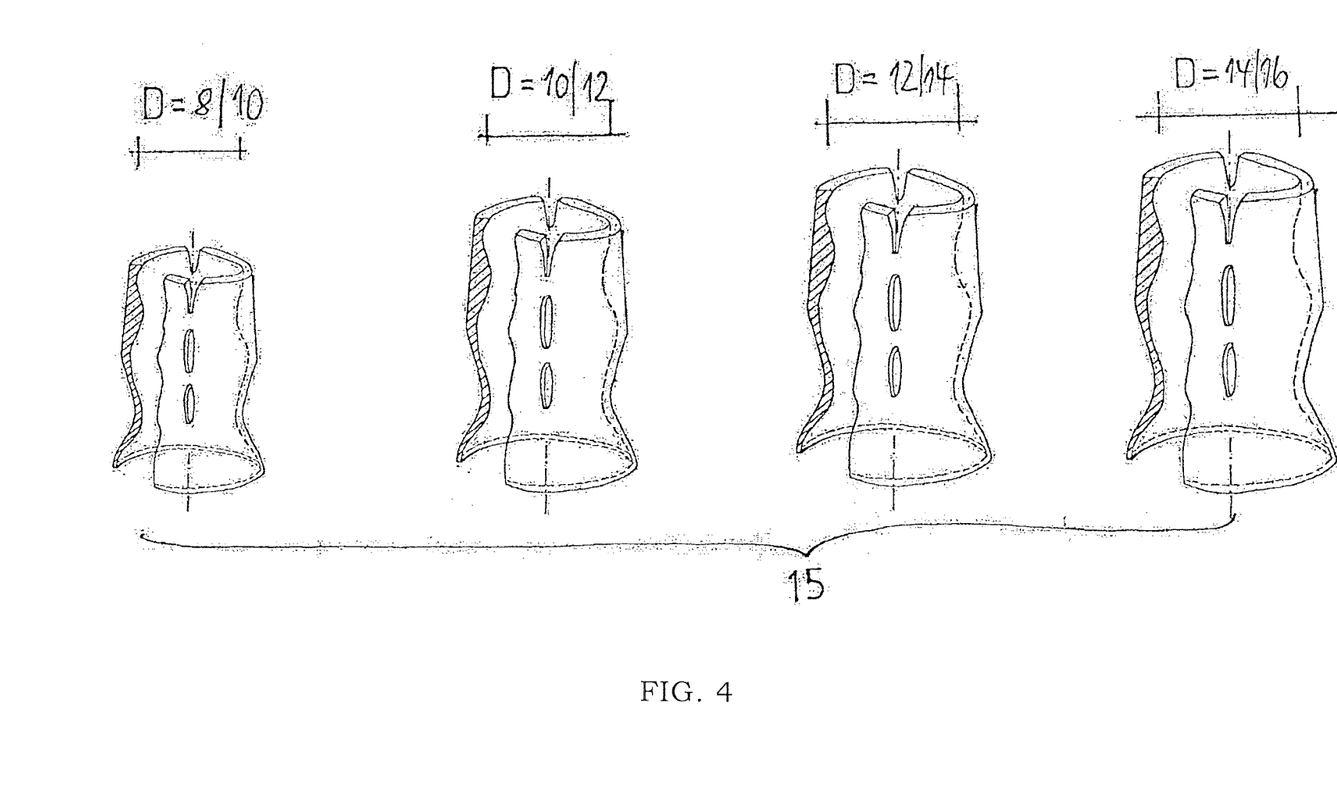
FIG. 4 shows an example of a group of assembled sample adapters.

FIG. 4 shows by way of example a group 15 of sample adapters, the diameters of which are graduated with respect to each other.

The graduation is selected such that all current lengths, diameters and angles of commercially available joint prostheses can be covered.

| List of reference | |
|---|---|
| shaft | 1 |
| neck | 2 |
| external cone | 3 |
| adapter | 4 |
| ball of the joint | 5 |
| receptacle in 5 | 6 |
| internal cone of 6 | 7 |
| moulded body | 8 |
| inner wall section of 8 | 9 |
| convex bulge | 10 |
| surface region where force is introduced | 11 |
| outer wall section of 8 | 12 |
| elastic wall section | 13 |
| cut-outs in 8 | 14 |
| sample adapter | 15 |
| longitudinal axis of 8 | A |
| load-bearing region of 5 | B |
| upper diameter of 4 | DO |
| lower diameter of 4 | DU |
| axial force | $F_A$ |
| physiological force | $F_R$ |
| spring force on external cone 3 | FS |
| spring force on internal cone 7 | FK |
| cone angle | $\alpha, \beta$ |

The invention claimed is:

1. A joint prosthesis system comprising:
a shaft having a lower end and an upper end, the lower end configured to be implanted into a femur, and the upper end having a neck comprising an external cone;
a ball having an outer surface and an inner receptacle comprising an internal cone, the internal cone of the receptacle configured to receive the external cone of the neck;
an adapter press fit between the external cone of the neck and the internal cone of the receptacle, the adapter having an inner wall facing the external cone of the neck and an outer wall facing the internal cone of the receptacle;
wherein the ball has a radial thickness, the thickness extending between the internal cone of the receptacle and the outer surface of the ball;
wherein the inner wall of the adapter has a convex bulge opposite a portion of the ball that has the greatest radial thickness; and
wherein the bulge areally concentrates force transmission between the shaft and the ball to a load bearing region adjacent the portion of the ball that has the greatest radial thickness, and target concentrates force transmission between the shaft and the ball to a narrow surface region of the neck.

2. The joint prosthesis system of claim 1, wherein the bulge is smoothly curved.

3. The joint prosthesis system of claim 1, wherein the bulge extends circumferentially from the inner wall of the adapter.

4. The joint prosthesis system of claim 3, wherein opposite the bulge, the outer wall of the adapter is planar with respect to the internal cone of the receptacle.

5. The joint prosthesis system of claim 1, wherein the adapter further comprises at least one elastic wall section longitudinally spaced from the bulge and bowed radially inwardly toward the external cone of the neck so that at least one gap exists between the adapter and the external cone of the neck and at least one gap exists between the elastic wall section and the internal cone of the receptacle.

6. The joint prosthesis system of claim 5, wherein the bulge faces an upper portion of the neck and the elastic wall section faces a lower portion of the neck.

7. The joint prosthesis system of claim 1, wherein the adapter comprises a superelastic material.

8. The joint prosthesis system of claim 7, wherein the superelastic material is a nickel-titanium alloy.

9. The joint prosthesis system of claim 1, wherein the adapter comprises a conical moulded body.

10. The joint prosthesis system of claim 9, further comprising at least one longitudinally extending cutout in the cortical moulded body.

11. The joint prosthesis system of claim 10, wherein the at least one longitudinally extending cutout is a slit.

12. The joint prosthesis system of claim 9, wherein the conical moulded body extends at an angle that corresponds to one of an angle of the external cone of the neck and an angle of the internal cone of the receptacle.

13. The joint prosthesis system of claim 9, wherein a length of the conical moulded body corresponds to a length of the external cone of the neck.

14. The joint prosthesis system of claim 9, wherein a diameter of the conical moulded body corresponds to a diameter of the external cone of the neck.

15. The joint prosthesis system of claim 9, further comprising a plurality of conical moulded bodies having different respective lengths, diameters, and angles that form a group of adapters, wherein the group of adapters is assigned a sample adapter for testing a fit between the shaft and the ball.

16. A joint prosthesis system comprising:
a shaft having a lower end and an upper end, the lower end configured to be implanted into a femur, and the upper end having a neck comprising an external cone;
a ball having an inner receptacle comprising an internal cone, the internal cone of the receptacle configured to receive the external cone of the neck; and an adapter press fit between the external cone of the neck and the internal cone of the receptacle, the adapter comprising a curvilinear inner wall facing the external cone the neck and a curvilinear outer wall facing the internal cone of the receptacle, wherein the joint prosthesis system further comprises at least one gap between the curvilinear outer wall of the adapter and the internal cone of the receptacle and at least one gap between the curvilinear inner wall of the adapter and the external cone of the neck.

17. The joint prosthesis system of claim 9, further comprising:

a lowermost end of the adapter that bears against the internal cone of the receptacle;

an elastic wall section in the adapter above the lowermost end, an upper portion and a lower portion of the elastic wall section bearing against the internal cone of the receptacle and a middle portion of the elastic wall section bearing against the external cone of the neck, thereby forming the at least one gap between the curvilinear outer wall of the adapter and the internal cone of the receptacle; and a bulge in the adapter above the elastic wall section, wherein at the bulge, the outer wall of the adapter is planar with respect to the internal cone of the receptacle and the inner wall of the adapter is convexly curved, thereby forming the at least one gap between the curvilinear inner wall of the adapter and the external cone of the neck.

18. A joint prosthesis system comprising:

a shaft having a lower end and an upper end, the lower end configured to be implanted into a femur, and the upper end having a neck comprising an external cone;

a ball having an inner receptacle comprising an internal cone, the internal cone of the receptacle configured to receive the external cone of the neck; and an adapter press fit between the external cone of the neck and the internal cone of the receptacle, the adapter having at least one elastic wall section bowed radially inwardly toward the external cone of the neck;

wherein an upper portion and a lower portion of the at least one elastic wall section bears only against the internal cone of the receptacle and a middle portion of the at least one elastic wall section bears only against the external cone of the neck, wherein the joint prosthesis system further comprises a smoothly curved convex bulge on the inner wall of the adapter that is longitudinally spaced from the elastic wall section; and wherein at least one gap is defined between the elastic wall section and the external cone of the neck and at least one gap exists between the elastic wall section and the internal cone of the receptacle.

* * * * *